United States Patent [19]
Day

[11] Patent Number: 4,891,518

[45] Date of Patent: Jan. 2, 1990

[54] APPARATUS FOR DETECTING A PLURALITY OF GASES

[75] Inventor: Stephen Day, Trumbull, Conn.

[73] Assignee: The Foxboro Company, Foxboro, Mass.

[21] Appl. No.: 87,872

[22] Filed: Aug. 21, 1987

[51] Int. Cl.$^4$ .............................................. G01J 1/00
[52] U.S. Cl. ..................................... 250/339; 250/343
[58] Field of Search ................................ 250/339, 343

[56] References Cited

U.S. PATENT DOCUMENTS 4,264,814 4/1981 Freund et al. ...................... 250/343
4,549,080 10/1985 Baskins et al. ...................... 250/343

*Primary Examiner*—Janice A. Howell

*Attorney, Agent, or Firm*—Thomas R. Morrison; Jules Jay Morris

[57] ABSTRACT

A gas detector for detecting a combination of at least three gasses employs an optical filter having a spectral passband shaped and positioned to produce substantially equal responses from a single detector to a given concentration of any single one of the gasses or to a concentration any two or more of the gasses. A filter spectrum encloses substantially equal areas of the absorption spectra of the gasses. The filter includes a spectral bandwidth, cut-on maximum wavelength, cut-on slope, cut-off maximum wavelength and cut-off slope, adjusted for controlling the areas of the gas absorption spectra enclosed therein.

4 Claims, 4 Drawing Sheets

APPARATUS FOR DETECTING A PLURALITY OF GASES

BACKGROUND OF THE INVENTION

The present invention relates to detectors and, more particularly, to detectors capable of detecting the presence of a gas by measuring a reduced transmission of a radiant energy caused by its absorption by the gas in a transmission path.

Gas detectors are known in which an emitter projects a beam of radiant energy through a column of a gas to be examined. A detector responds to radiant energy emerging from the column of gas to produce an electrical signal. The column of gas absorbs the radiant energy at wavelengths characteristic of the type of gas and with an absorption magnitude proportional to the amount of the gas in the column of gas.

Some gas detectors are employed to detect the presence of a particular gas while ignoring absorption from all other gasses. Such discrimination between desired and undesired gasses is attained by employing a selective filter in the beam of radiant energy effective to pass that portion of the spectrum in which the target gas is known to absorb radiant energy and to block substantially all other portions of the spectrum. Provided that the absorption spectrum of the target gas is reasonably well isolated in wavelength from the spectra of other gasses which might exist in the atmosphere, such a single-gas detector is quite effective.

The present invention seeks to provide apparatus for detecting the presence of a plurality of related gasses such as, for example, a plurality of fluorocarbon gasses. Such fluorocarbon gasses have absorption characteristics exhibiting overlapping absorption spectra. Thus, detection is complicated by interference among the overlapping spectra. For detection of a single pair of gasses, one might employ a filter positioned at a wavelength coinciding with the crossover between the two absorption spectra. The detector output in such a system is a reasonable approximation of the gas concentration, without concern for which one of the pair of gasses produces the absorption.

When the number of gasses to be detected rises to more than two, the spectra are generally so disordered that it has generally been considered impossible to find a single spectral region in which absorption from all of the gasses of interest are about equal.

In one application, any one or more of as many as four or five fluorocarbon gasses may escape to the environment. In a shipboard environment, for example, fluorocarbons 11, 12, 113 and 114 may be used. Fluorocarbons, being heavier than air, may accumulate in lower portions of the vessel. Since they are colorless and odorless, their presence may not be detected. Personnel working in an environment containing a significant concentration of any of the fluorocarbons may suffer oxygen deprivation and, in an extreme case, may become asphyxiated.

From the standpoint of personnel safety, all of the fluorocarbons of interest have about the same effect. That is, a concentration of fluorocarbon 11, for example, has about the same effect as the same concentration of any of the other fluorocarbons of interest. Furthermore, the presence of two or more fluorocarbons are additive in their effect. Two of the above fluorocarbons, both having the same concentration, produce about the same physiological effect as twice the concentration of either.

It would thus be desirable to have a fluorocarbon detector responsive to the fluorocarbons of interest, either alone or in any additive combination. Such a detector should have an alarm device responsive to the total concentration of all of the fluorocarbons of interest, and be substantially non-responsive to other gasses expected to co-exist in the environment.

OBJECTS AND SUMMARY OF THE INVENTION

It is an object of the invention to provide a detector responsive to a plurality of fluorocarbon gasses which overcomes the drawbacks of the prior art.

It is a further object of the invention to provide a detector responsive to the presence of a plurality of fluorocarbon gasses wherein an optical filter includes a passband having a spectral bandwidth accommodating one absorption peak of each of the plurality.

It is a still further object of the invention to provide a detector employing an optical filter having a passband positioned with respect to the absorption spectra of a plurality of fluorocarbon gasses such that cut-on and cut-off wavelengths substantially equalize the detector response to concentrations of each of the gasses.

Briefly stated, the present invention provides a gas detector for detecting a combination of at least three gasses employing an optical filter having a spectral passband shaped and positioned to produce substantially equal responses from a single detector to a given concentration of any single one of the gasses or to a concentration any two or more of the gasses. A spectral passband encloses substantially equal areas of the absorption spectra of the gasses. The filter includes a spectral bandwidth, cut-on maximum wavelength, cut-on slope, cut-off maximum wavelength and cut-off slope, adjusted for controlling the areas of the gas absorption spectra enclosed therein.

According to an embodiment of the invention, there is provided a gas detection apparatus for detecting at least three gasses, the at least three gasses including absorption spectra each having at least one absorption maximum comprising: a source of a radiant energy, the source of radiant energy having a band of wavelengths substantially broader than a spectral region containing the at least one absorption maximum for each of the gasses, a sample cell, means for admitting the radiant energy into the sample cell, a detector, means for impinging the radiant energy onto the detector after the radiant energy passes at least once along a path through the sample cell, means for drawing a sample of a gas into the sample cell for determining a presence of one or more of the gasses, filter means for filtering the radiant energy, the filter means having a filter spectrum including a cut-on slope, a cut-on maximum, a cut-off maximum and a cut-off slope, and the filter spectrum enclosing substantially equal areas of absorption spectra of the gasses, whereby the detector is enabled to respond to a sum of the at least three gasses in the path.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
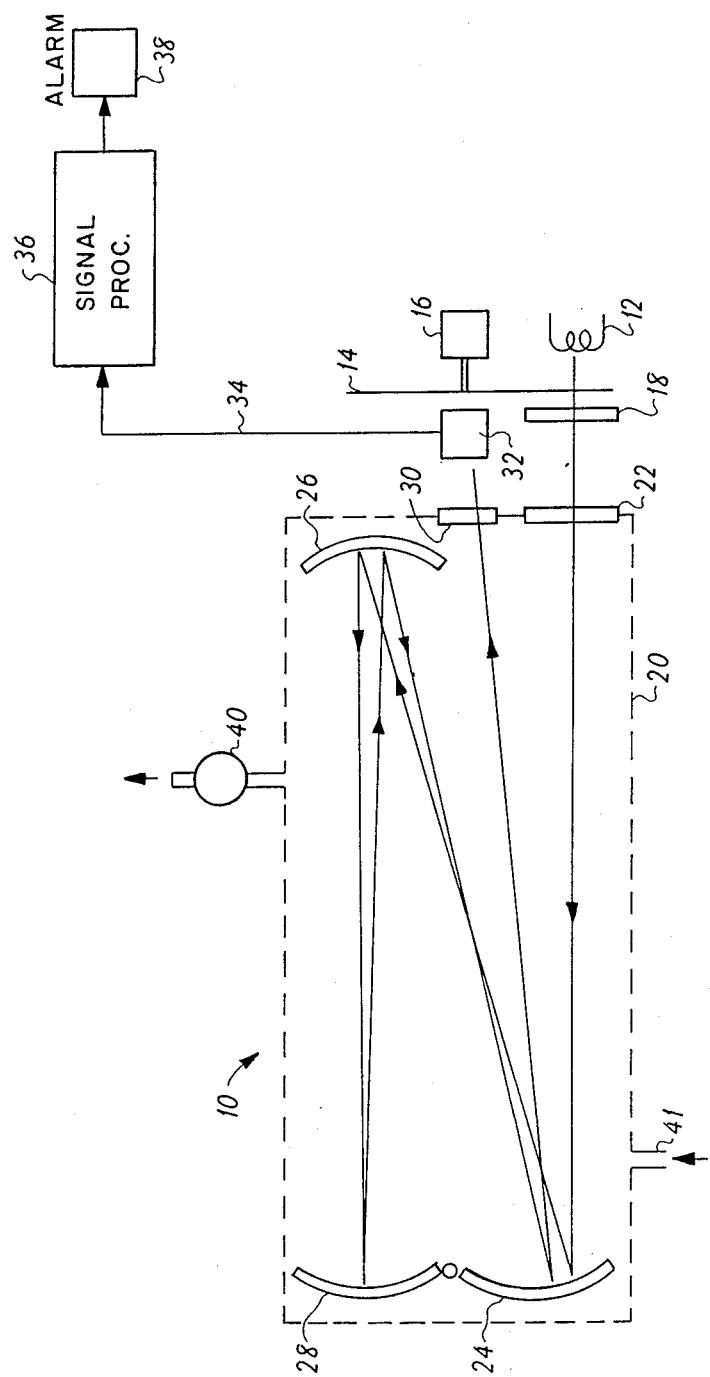
FIG. 1 is a simplified schematic diagram of a gas detector according to an embodiment of the invention.

Referring first to FIG. 1, there is shown, generally at 10, a gas detector suitable for use with an embodiment of the present invention. A source of radiant energy such as, for example, a lamp filament 12, is heated to a temperature effective for generating radiant energy in a band appropriate for a gas or gasses to be detected. Many gasses of interest have absorption spectra in the infra-red range of 8.7 to 14 micrometers. Accordingly, lamp filament 12 is preferably heated by a source of electricity to a temperature providing a substantial radiance in that spectral range.

A conventional chopper disk 14, rotated by an electric motor 16, includes one or more apertures therein to intercept periodically the radiant energy from lamp filament 12. An optical filter 18 passes a band of wavelengths of the radiant energy impinging upon it and substantially blocks the remainder of the radiant energy from lamp filament 12.

A sample cell 20 includes an input window 22 permitting the filtered radiant energy from optical filter 18 to enter. A plurality of mirrors 24, 26 and 28 within sample cell 20 fold an optical path of the radiant energy therein to multiply the effective length through which the radiant energy must pass before it reaches an output window 30. A detector cell 32, of any conventional type, receives the radiant energy passing through output window 30 and produces an electrical signal having an amplitude related to the amount of radiation falling upon it. The electrical signal is applied on a line 34 to a conventional signal processor 36. Signal processor 36 may employ one or more amplifiers and threshold devices to produce an alarm signal in response to a predetermined condition of the signal produced by detector cell 32. An alarm device 38, which may include, for example, one or more analog meters, alert and warning lamps, or audible alarm devices, receives the output from signal processor 36 for producing a signal effective for alerting nearby personnel of the detected condition. In addition to the alerting and alarming function, alarm device 38 may also include hard-copy or electronic data recording devices for permanent storage of a detected condition.

A sample pump 40 draws ambient air into sample cell 20 through an air inlet 41, whereby the optical path in sample cell 20 includes a sample of the ambient air including possible contaminants of interest. As is conventional, a flexible tube and wand probe (not shown) may be connected to air inlet 41 for localizing a source of an air sample.

One skilled in the art would recognize that mirrors 24, 26 and 28 are convenient for increasing the optical path without increasing the physical dimensions of sample cell 20 but are not a necessary part of the apparatus. The apparatus shown provides an optical path folded to make six passes through the sample in sample cell 20 between input window 22 and output window 30. Corresponding results could be attained using a longer sample cell having an input window at one end and an output window at the other end to form the same optical path length.

Figure 2:
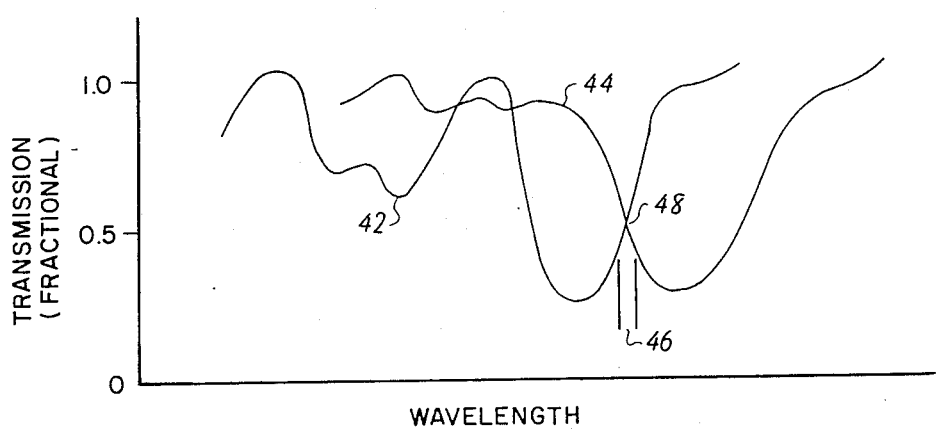
FIG. 2 shows two absorption spectra to which reference is made in describing the problem to be solved by the present invention.

Referring now to FIG. 2, there is shown a first absorption curve 42 of a first gas superimposed on a second absorption curve 44 of a second gas. A detector covering the entire band of wavelengths illustrated in FIG. 2 could be calibrated to provide an output representing the concentration of one of the gasses if the other were not present. It will be noted, however, that the shapes of the absorption curves 42 and 44 are quite different. Accordingly, equal concentrations of the two gasses taken alone, would produce substantially different detector responses.

One possible solution may be to employ a narrow-band filter having a passband 46 centered on a common crossover 48 between the two absorption curves 42 and 44. If the slopes of the absorption curves are about equal in the vicinity of crossover 48, a detector receiving radiant energy filtered by a filter having a passband corresponding to passband 46 could produce an output signal accurately responsive to the sum of the concentrations of either one or both of the two gasses having absorption curves 42 and 44.

The problem becomes more difficult in an apparatus for detecting more than two gasses. In general, it is not possible to find a single spectral region in which the absorption of three or more gasses is about equal. One specific problem prompting the present invention is that of detecting any one or more of a plurality of related gasses, namely, fluorocarbons. Since these gasses are similar in molecular structure, it was discovered that their molecular rotational and vibrational modes leading to absorption spectra are more closely allied than is the case for gasses in general. In the prior art, recognition was made of the relationships between the absorption spectra of these gasses to produce one technique for the detection of any one, two or three or more selected fluorocarbon gasses with a single detector.

Figure 3:
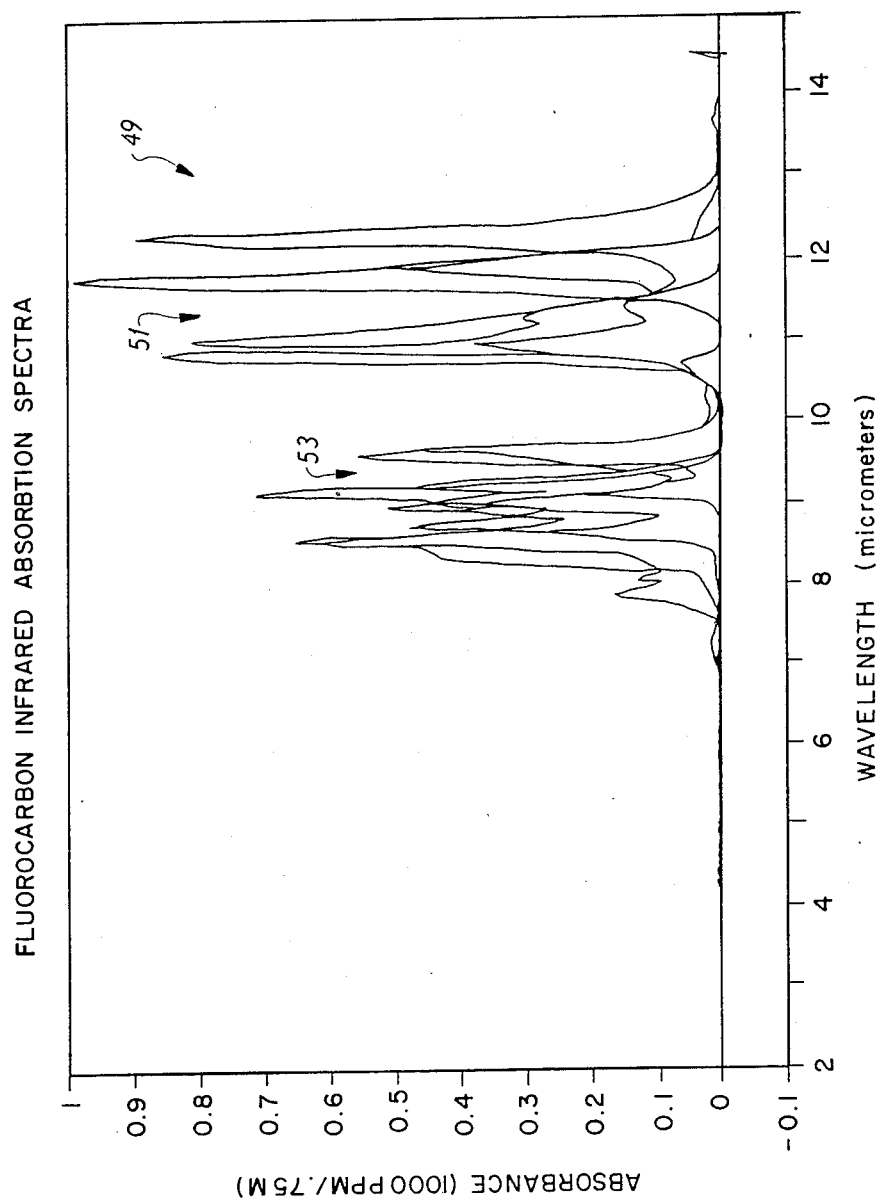
FIG. 3 shows absorption spectra of four fluorocarbons superimposed on one another with two spectral regions of interest indicated by arrows.

Referring now to FIG. 3, there is shown, generally at 49, superimposed absorption spectra of four fluorocarbon gasses 11, 12, 113 and 114. Two spectral regions 51 and 53 are identified by arrows in preparation for the following discussion.

Figure 4:
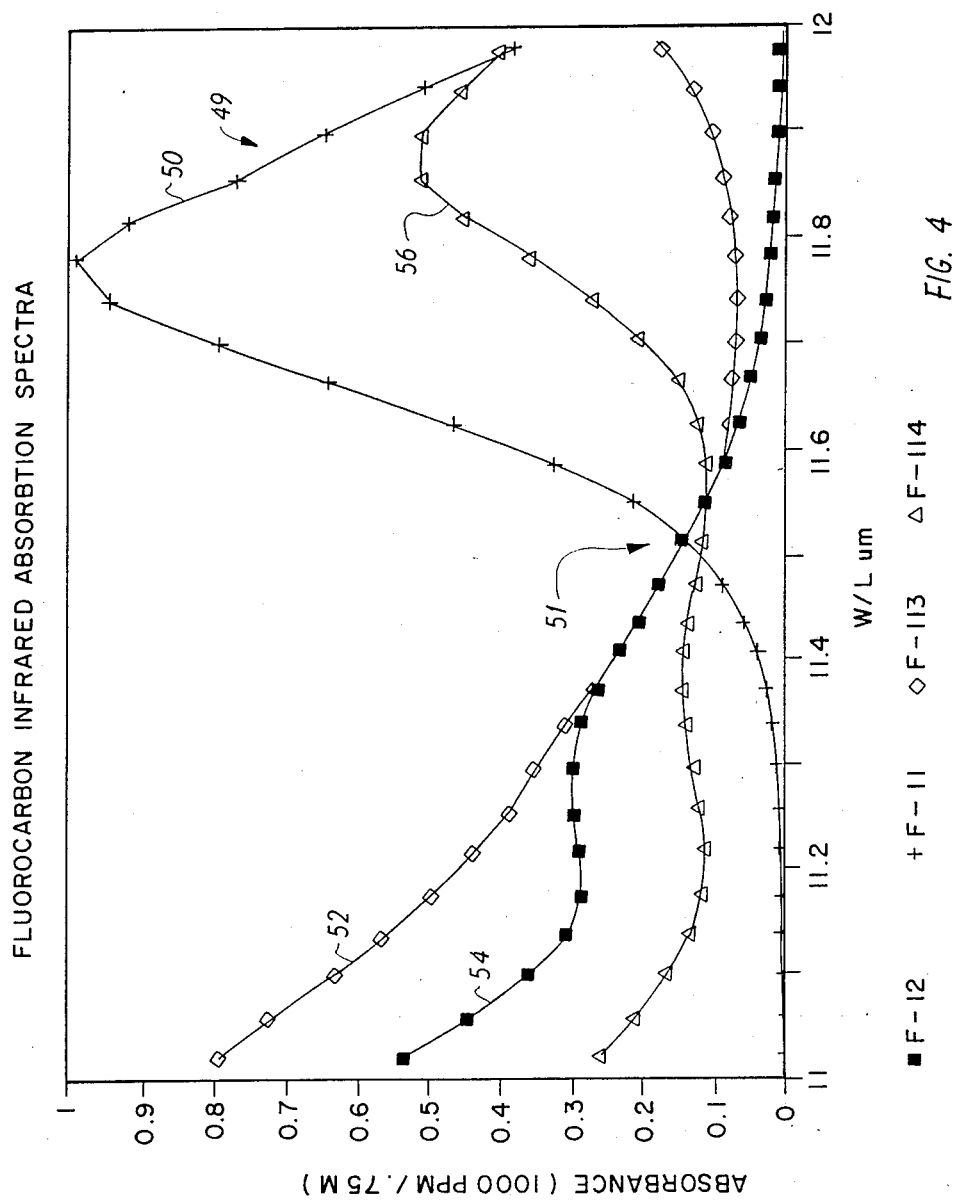
FIG. 4 shows an enlarged view of one of the spectral regions of FIG. 3.

Referring now to FIG. 4, spectral region 51, when greatly enlarged, includes absorption curves 50, 52, 54 and 56 all of which pass reasonably close to each other in the vicinity of 11.49 micrometers. It will be noted that their slopes are markedly different. Such slope differences can lead to unacceptably large measurement errors under normal circumstances. However, it was discovered that narrowing the optical bandwidth of optical filter 18 (FIG. 1), centered on 11.49 micrometers, to a half-height bandwidth of 0.2 micrometers, enabled detection of the cumulative amounts of any one, two, three or four of the fluorocarbons with an error of no worse than 20 percent.

Thus, an apparatus for detecting a plurality of related gasses was found. It was discovered that the bandwidth of optical filter 18 should be about 1.5 percent of the peak wavelength, but that accuracy was not critically dependent on this parameter. The spectral position of the peak wavelength, in contrast is critical. The peak wavelength within about 0.2 percent of 11.49 micrometers is required to the desired measurement accuracy. Although such accuracy is attained in the laboratory, and the resulting device operates satisfactorily, it was discovered that commercial sources of optical filter 18 are unable to guarantee the required accuracy of the peak wavelength.

Notwithstanding the difficulty in producing a suitable optical filter 18 for a narrow-bandwidth embodiment, such apparatus for detecting the fluorocarbons identified above has been made, sold and in public use for more than a year prior to the filing date of the present application. Thus, such a narrow-bandwidth device is considered to be the closest prior art.

Figure 5:
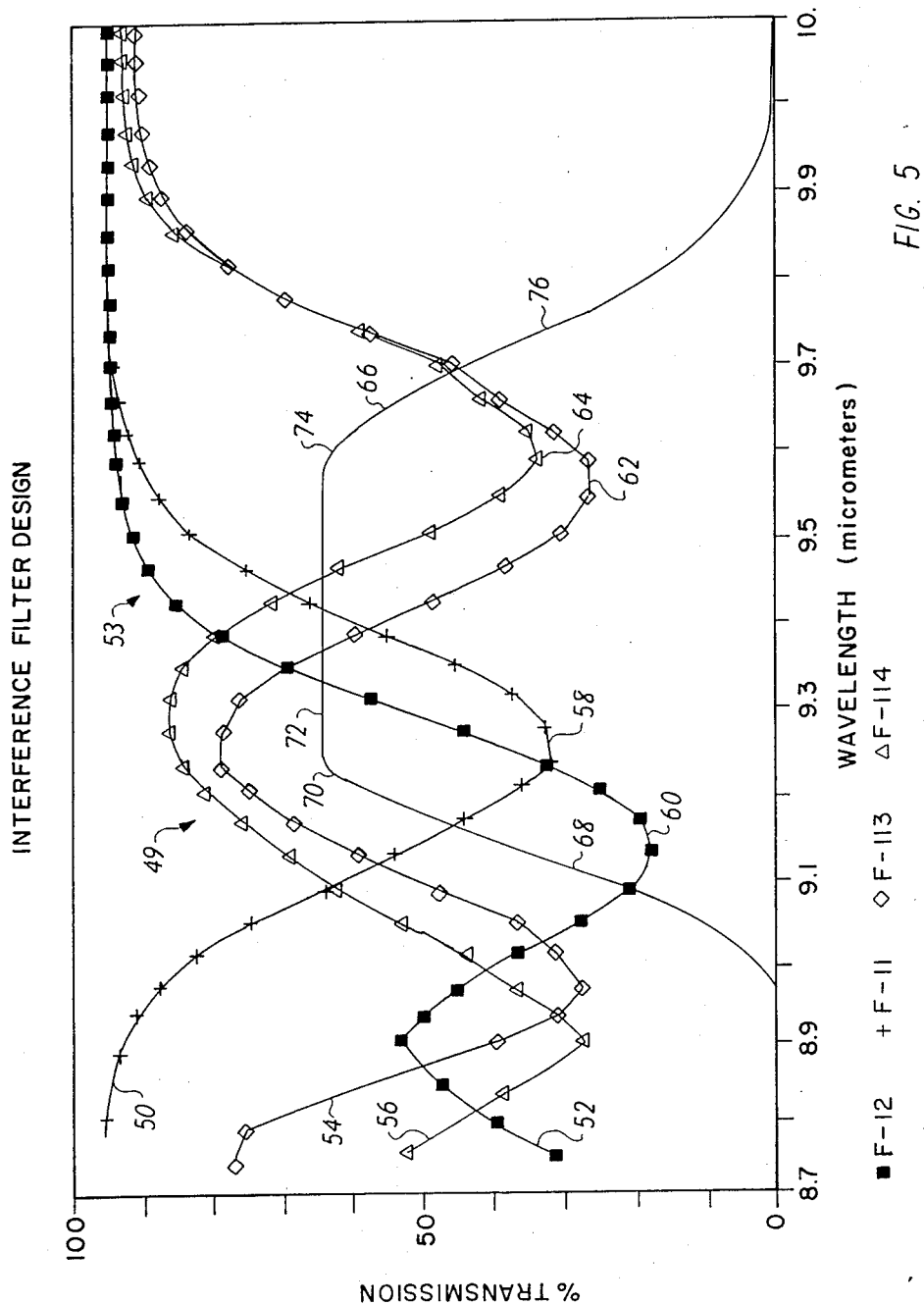
FIG. 5 shows an enlarged view of the other of the spectral regions of FIG. 3.

Referring now to FIG. 5, in spectral region 53, it was discovered that absorption curves 50, 52, 54 and 56 of fluorocarbons 11, 12, 113 and 114, respectively, although lacking the common crossover point in spectral region 51 (FIG. 4) nevertheless contained characteristics rendering the four gasses detectable with acceptable errors. All four of the fluorocarbons of interest, due to their similar molecular structures, include absorption maxima 58, 60, 62 and 64 between about 9.13 and about 9.59 micrometers. In addition, the shapes of all of absorption curves 50, 52, 54 and 56 about absorption maxima 58, 60, 62 and 64 are quite similar to each other. The magnitudes of absorption maxima 58, 60, 62 and 64 are not equal, however. The absorption indicated by absorption maximum 60 is much greater than any of the others. In addition, the absorption indicated by absorption maximum 62 is greater than absorption maximum 58 which is, in turn, slightly greater than absorption maximum 64. Thus, according to conventional wisdom, detection of these gasses in any combination is not possible.

It was discovered that an optical filter 18 (FIG. 1) having suitable cut-on and cut-off wavelengths together with suitable cut-on and cut-off slope constants is capable of producing an output from a single detector cell 32 responsive to the concentration of any one of the gasses, or the sum of the concentrations of any of the four gasses in any combination, within an accuracy of about 11 percent. Such an accuracy is well with the acceptable range for some detector applications.

In the direction of increasing wavelength, filter spectrum 66 includes a cut-on slope 68 reaching a maximum at a cut-on peak 70, a generally flat passband 72 to a cut-off peak 74 and a cut-off slope 76. The illustrated spectral positioning of filter spectrum 66 results in cut-on slope 68 intercepting portions of absorption curves 50 and 52 on the short-wavelength sides of their absorption maxima 58 and 60, respectively. The areas between absorption curves 50 and 52 and filter spectrum 66 are about equal, whereby the responses of detector cell 32 to the two gasses producing these absorption spectra are about equal for equal concentrations. Similarly, cut-off slope 76 intercepts absorption curves 54 and 56 on the long-wavelength sides of absorption maxima 62 and 64. The areas between these curves and filter spectrum 66 are also about equal to each other and to areas between absorption curves 50 and 52 and filter spectrum 66. Thus, detector cell 32 (FIG. 1) is enabled to respond to one, or the sum of two, three or four of the fluorocarbons with acceptable accuracy.

A comparison of the two techniques illustrated in FIGS. 4 and 5 reveals the basic differences between the techniques. In the narrow-band case of FIG. 4, a common crossover must exist found wherein all of the gasses of interest have closely related absorptivities centered on 11.49 micrometers. Thus, in this spectral region, a filter, accurately centered on 11.49 micrometers, and with a spectral bandwidth of about 1.5 percent of the central spectral value, reduced the error effects of the disparity of spectral shapes spaced further away from the central spectral value to about 20 percent.

A similar common crossover is not evident elsewhere in the absorption spectra of the four gasses of interest in FIG. 5 nor, in general, in the spectra of combinations of other gasses. However, in the region of 9.13 to 9.59 micrometers for the fluorocarbons of interest, a much broader filter window is effective for enclosing substantially equal areas of the absorption spectra of the four gasses by positioning and shaping the cut-on and cut-off filter slopes. The broader filter window is capable of reducing measurement errors to about 11 percent. Besides cutting measurement errors nearly in half, the broader window has tolerances more amenable to economical manufacture.

Although the present invention is described in the environment of measurement of related gasses, namely fluorocarbons, such description should not be considered to form a limiting part of the invention. It may be possible to discern portions of the spectra of at least three gasses, at least one of which may be unrelated to the other two, in which the techniques disclosed in the present invention may be employed. What is required for success in such a combination is a spectral region in which the detector response can be shaped using cut-on slope, cut-on maximum wavelength, cut-off maximum wavelength and cut-off slope to encompass substantially equal areas of the spectra of the at least three gasses. Thus, the present invention should be considered to cover detection of such a combination of gasses wherein at least one may be unrelated to the other two.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What I claim is:

1. A gas detection apparatus for detecting at least three gasses, said at least three gasses including absorption spectra each having at least one absorption maximum comprising:

a source of a radiant energy;

said source of radiant energy having a band of wavelengths substantially broader than a spectral region containing said at least one absorption maximum for each of said gasses;

a sample cell;

means for admitting said radiant energy into said sample cell;

a detector;

means for impinging said radiant energy onto said detector after said radiant energy passes at least once along a path through said sample cell;

means for drawing a sample of a gas into said sample cell for determining a presence of one or more of said gasses;

filter means for filtering said radiant energy;

said filter means having a filter spectrum including a cut-on slope, a cut-on maximum, a cut-off maximum and a cut-off slope; and said filter spectrum enclosing substantially equal areas of absorption spectra of said gasses, whereby said detector is enabled to respond to a sum of said at least three gasses in said path.

2. A gas detection apparatus according to claim 1 wherein:

said at least three gasses include at least three fluorocarbon gasses; and said filter spectrum extends from about 8.9 to about 10.0 micrometers.

3. A gas detection apparatus according to claim 2 wherein said cut-on maximum is about 9.22 micrometers and said cut-off maximum is about 9.6 micrometers.

4. A gas detection apparatus according to claim 1 wherein at least one of said cut-on slope and said cut-off slope intersects an absorption spectrum of at least one of said plurality of gasses, said at least one of said cut-on slope and said cut-off slope at least partly controlling an area of said absorption spectrum of at least one of said plurality of gasses to reduce a contribution of said absorption spectrum at said detector to be substantially equal to contributions of absorption spectra of a remainder of said plurality of gasses whereby, said substantially equal areas are attained.

* * * * *